(12) United States Patent
Nachman et al.

(10) Patent No.: US 11,793,458 B2
(45) Date of Patent: Oct. 24, 2023

(54) TRACKING CALORIC EXPENDITURE USING SENSOR DRIVEN FINGERPRINTS

(71) Applicant: Intel Corporation, Santa Clara, CA (US)

(72) Inventors: Lama Nachman, Santa Clara, CA (US); Hong Lu, Santa Clara, CA (US); Jennifer Healey, San Jose, CA (US); Rahul C. Shah, San Francisco, CA (US); Jonathan J Huang, Pleasanton, CA (US); Rita H Wouhaybi, Portland, OR (US); Giuseppe Raffa, Portland, OR (US)

(73) Assignee: Intel Corporation, Santa Clara, CA (US)

( * ) Notice: Subject to any disclaimer, the term of this patent is extended or adjusted under 35 U.S.C. 154(b) by 1958 days.

(21) Appl. No.: 15/084,670

(22) Filed: Mar. 30, 2016

(65) Prior Publication Data
US 2017/0281079 A1   Oct. 5, 2017

(51) Int. Cl.
| | |
|---|---|
| A63B 22/02 | (2006.01) |
| H04W 4/029 | (2018.01) |
| A61B 5/00 | (2006.01) |
| H04L 67/306 | (2022.01) |
| A61B 5/11 | (2006.01) |
| A61B 5/22 | (2006.01) |
| A61B 5/117 | (2016.01) |
| A63B 71/06 | (2006.01) |

(52) U.S. Cl.
CPC .......... *A61B 5/4866* (2013.01); *A61B 5/117* (2013.01); *A61B 5/1118* (2013.01); *A61B 5/222* (2013.01); *A63B 22/02* (2013.01); *H04L 67/306* (2013.01); *A63B 71/0622* (2013.01); *A63B 2071/0625* (2013.01); *A63B 2071/0658* (2013.01); *A63B 2220/12* (2013.01); *A63B 2220/20* (2013.01); *A63B 2220/40* (2013.01); *A63B 2220/805* (2013.01); *A63B 2220/806* (2013.01); *A63B 2225/50* (2013.01); *A63B 2230/75* (2013.01); *H04W 4/029* (2018.02)

(58) Field of Classification Search
None
See application file for complete search history.

(56) References Cited

U.S. PATENT DOCUMENTS

| | | | | |
|---|---|---|---|---|
| 8,718,672 | B2 * | 5/2014 | Xie | G01C 22/00 455/456.1 |
| 9,393,460 | B1 * | 7/2016 | Emigh | A61B 5/103 |

(Continued)

*Primary Examiner* — Michael J Dalbo
*Assistant Examiner* — Denise R Karavias
(74) *Attorney, Agent, or Firm* — Schwegman Lundberg & Woessner, P.A.

(57) ABSTRACT

System and techniques for tracking caloric expenditure using sensor driven fingerprints are described herein. A set of outputs may be obtained from a plurality of sensors. A fingerprint may be generated using the set of outputs. The fingerprint may correspond to an activity observed by the plurality of sensors. The generated fingerprint may be compared to a set of fingerprints stored in a database. Each fingerprint of the set of fingerprints may correspond to a respective caloric expenditure. A caloric expenditure may be calculated for the activity based on the comparison. An exercise profile of a user may be updated using the caloric expenditure.

24 Claims, 5 Drawing Sheets

(56) References Cited

U.S. PATENT DOCUMENTS

| | | | | |
|---|---|---|---|---|
| 2004/0152957 A1* | 8/2004 | Stivoric | ............... | A61B 5/1118 |
| | | | | 128/903 |
| 2005/0113650 A1* | 5/2005 | Pacione | ............... | A61B 5/4866 |
| | | | | 600/300 |
| 2011/0087137 A1* | 4/2011 | Hanoun | ............... | G06F 19/3418 |
| | | | | 600/587 |
| 2013/0217979 A1* | 8/2013 | Blackadar | ............ | A61B 5/6829 |
| | | | | 600/301 |
| 2014/0330408 A1* | 11/2014 | Rolley | ................... | G16H 10/60 |
| | | | | 700/91 |
| 2015/0289797 A1* | 10/2015 | Pacione | ............... | A61B 5/4812 |
| | | | | 600/301 |
| 2018/0169475 A1* | 6/2018 | Nam | ................. | A63B 24/0006 |

\* cited by examiner

TRACKING CALORIC EXPENDITURE USING SENSOR DRIVEN FINGERPRINTS

TECHNICAL FIELD

Embodiments described herein generally relate to tracking caloric expenditures for activities and more particularly, but without limitation, to tracking caloric expenditures for activities using sensor driven fingerprints.

BACKGROUND

Fitness devices may collect data from an accelerometer and/or a heart rate sensor to detect physical activities and map them to a caloric expenditure for continuous tracking (e.g., fitness trackers, etc.). Fitness devices tend to be accurate in identifying caloric expenditures by combining a measured heart rate with accelerometer data.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
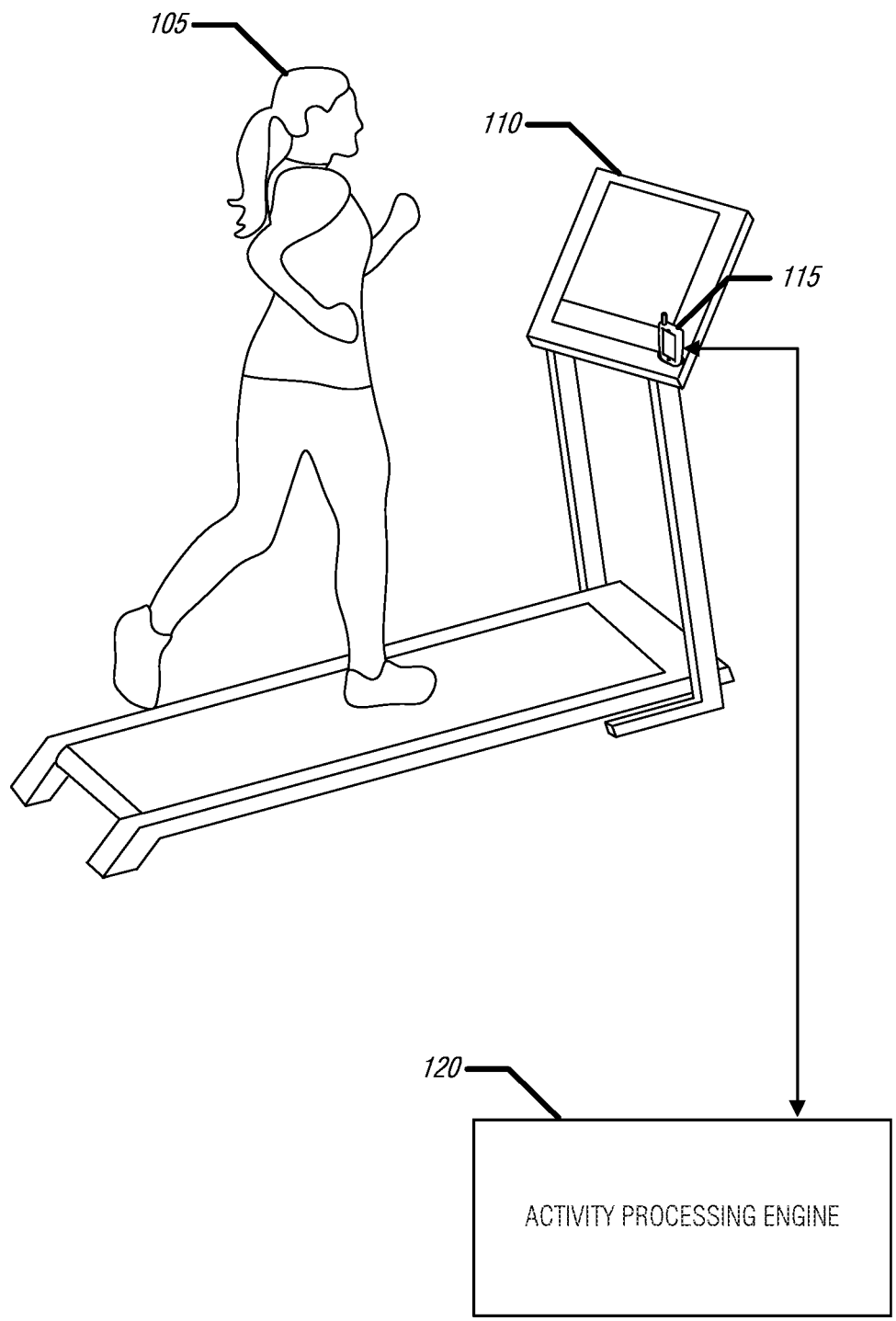
FIG. 1 is a block diagram of an example of an environment including a system for tracking caloric expenditure using sensor driven fingerprints, according to an embodiment.

The systems and techniques discussed herein address the problem of how to calculate accurate caloric expenditure estimates when a person is not wearing a wearable fitness device (wristband, watch, etc.) or other movement tracking device. While wearable fitness devices may provide accurate estimates of a person's caloric expenditure during an activity, portable devices (e.g., smart phone, tablet, etc.) may be more widely used than wearable fitness devices as people tend to keep them close during a wide variety of activities.

When people exercise at the gym or elsewhere (e.g., parks, outdoor trails, etc.), they may not have the wearable fitness device on them. They also may not have the portable device on their body. For example, the portable device may be sitting on a display of a piece of gym equipment (e.g., to listen to music, watch videos, read content, etc.). In such cases, the sensors of the portable device may not be able to directly sense the movement of the person engaging in an activity with more than limited fidelity. In such cases, the person's movements may not be recorded accurately and an estimated caloric expenditure for the movement may be inaccurate (e.g., underestimated).

The present subject matter solves this problem by substituting proxy data (e.g., sensor data collected about the environment corresponding with the person, about other objects in the environment corresponding with the person, etc.) for the missing wearable data to better estimate caloric expenditure. For example, previously collected caloric expenditure data that best matches the users current state as matched by sensor data collected about the environment corresponding with the person may be used as proxy data. The present subject matter may bridge the gap between caloric expenditure estimations provided while wearing a wearable fitness device (e.g., with accelerometer, heart rate monitor, etc.) and an assumption of sedentariness of a user when not wearing the wearable fitness device.

The term "fingerprint" as used herein may refer to a unique pattern derived from one or more sensor inputs. Much like a human fingerprint, the data collected from sensors may provide a highly unique identifier. As used herein, fingerprints may be derived from a set of sensor inputs by using techniques such as, for example, using dimensional vectors. For example, a set of sensor inputs collected over a time period and each sensor's vectors may be mapped in an N-dimensional space. The map of the vectors in the N-dimensional space may be considered a fingerprint for the set of sensor inputs for the period of time.

The present subject matter may identify routines in a person's behavior that may be fingerprinted (e.g., generate a unique identifier, signature, etc.) using sensor data (e.g., location, time, computer network data, audio data, visual data, etc.) collected by a portable device (e.g., smartphone, tablet, etc.). The term fingerprint as used herein may refer to a unique pattern derived from one or more sensor inputs. During periods when both the portable device and the wearable fitness device is available, the estimated caloric expenditure for an activity captured from the wearable fitness device may be associated with a contextual activity fingerprint associated with a particular user, time of day, location, etc. In other times when the user only has the portable device, instead of defaulting to a sedentary caloric estimate, the portable device may find the most relevant activity fingerprint and may use the fingerprint to make a caloric assessment. A wide range of activities may be fingerprinted for example, running, using weight machines at the gym, and completing household chores. The sensors used to collect data used to generate a fingerprint for an activity may include, for example, an accelerometer, a gyroscope, a compass, a light sensor, an audio sensor, a Wi-Fi sensor, a GPS or other location sensor, a pressure sensor, and a camera.

A wearable fitness device may replace missing data segments (e.g., when a person is not wearing the wearable fitness device) with a baseline value of caloric expenditure (e.g., a caloric expenditure while sedentary) and may show that the user is sedentary or has no activity during such a time segment. Assuming a user is sedentary when not wearing the wearable fitness device may underestimate the user's caloric expenditure (e.g., when they are exercising at a gym and have forgotten the wearable fitness device at home, etc.).

The present subject matter may fuse a fingerprint for an activity with an estimated caloric expenditure and store the data as a reference fingerprint allowing the for better caloric expenditure estimations when the person is not wearing the wearable fitness device. When a fingerprint generated for a future activity matches the reference activity, the caloric expenditure may be used to calculate a caloric expenditure for the current activity. For example, the user may be at the gym, but has forgotten the wearable fitness device at home. In such a case, it may be identified that an activity is being performed using the sensor data and a more accurate caloric expenditure may be calculated for a time period corresponding to the activity by matching a fingerprint generated for the activity to a reference activity and using a caloric expenditure corresponding to the reference activity.

In another example, the user may go to the gym and have a wearable fitness device and a portable device for some number of days. The user may wear the wearable fitness device and put the portable device on a display of a treadmill, bike, etc. For each gym trip, the calories spent per minute as the user goes from one machine to another may be captured over a period of time along with a portable device sensor data fingerprint for the period of time using various sensor inputs (e.g., location of a piece of equipment, a vibration signature of the piece of equipment, an electromagnetic signature near the equipment, sound recorded by a microphone, and an image of the ceiling, a communication connection between the piece of equipment and the portable device, etc.). On successive trips to the gym, the user may repeat the same exercise while having the portable device in a similar location while conducting an activity (e.g., using the piece of equipment, etc.), and a fingerprint for an activity may be created based on matching a set of sensor data with the caloric expenditure for the activity. A per minute caloric expenditure value may then be assigned to the activity that is averaged over the multiple days of collected data. In some examples, an individual machine and/or activity may not be identified. However, it may be identified that the user is at the gym or at the weight room by matching sensor data from the portable device to a set of fingerprints. In such a case, an aggregate estimate may be substituted for time at the gym or time in the weight room based on an average caloric expenditure corresponding to a gym fingerprint or a weight room fingerprint.

In some examples, sensors may be deployed in the environment (e.g., in proximity to the user, in a piece of exercise equipment, in a kiosk, etc.) and may detect the user implicitly (e.g., using audio, other on-body devices, etc.) or explicitly (e.g., user login, etc.) in order to help with filling a more detailed view of where they are moving inside the gym and possibly which activity they are engaging in or what machine they are using. For example, the gym may have a terminal near a machine or workout station where the user may login to indicate that they are participating in an activity or using a machine. In another example, the gym may have sensors distributed throughout that may detect the user's activity and machine usage. In some examples, activities in a home or public place may be detected using context as a signature that may be matched to a fingerprint for previous sensed data that may carry more detailed sensed data including heart rate. If the user has never been in a context, they may be able to select another context and label them as similar or they may be automatically matched based on similarity with someone else with a similar profile (e.g., having similar caloric expenditure, similar heart rate, etc.).

FIG. 1 is a block diagram of an example of an environment 100 including a system for tracking caloric expenditure using sensor driven fingerprints, according to an embodiment. The environment 100 may include a user 105 that may be using a piece of exercise equipment 110 (e.g., treadmill, elliptical machine, etc.) upon which portable device 115 (e.g., a smartphone, tablet, etc.) may be placed. The portable device 115 may be communicatively coupled (e.g., via wireless network connection, locally executing, etc.) to an activity processing engine 120.

The user 105 may be engaged in an activity such as, for example, running on a treadmill. The portable device 115 may include a variety of sensors (e.g., accelerometer, GPS receiver, gyroscope, wireless transmitter, etc.). The sensors may detect a variety of environmental conditions (e.g., movement, sounds, video, etc.) within proximity of the user 105. For example, the sensors may detect movement of the piece of exercise equipment 110.

The activity processing engine 120 may collect data from each of the sensors over a period of time. The beginning of the period of time may be determined by a first change in sensor activity detected by the activity processing engine 120 (e.g., an increase in average acceleration, etc.). The end of the period of time may be determined by a second change (e.g., a decrease in average acceleration, etc.) in sensor activity detected by the activity processing engine 120. The sensor data for each sensor may be evaluated by the activity processing engine 120 to create a fingerprint (e.g., a unique pattern of received sensor inputs) for each sensor for the period of time. The fingerprints for each sensor may then be aggregated into an activity fingerprint for the period of time.

The activity processing engine 120 may compare the activity fingerprint to a set of reference activity fingerprints (e.g., a database of activity fingerprints, etc.). For example, the activity processing engine 120 may use pattern matching (e.g., Euclidian distance, cosine distance, KL divergence, etc.) to determine the similarity between the activity fingerprint vector and a reference fingerprint vector of each of the set of reference fingerprints to determine. A reference fingerprint may be selected based on the comparison. The selected reference fingerprint may correspond to a caloric expenditure per minute. For example, running on a treadmill may correspond to a caloric expenditure of 15 calories per minute.

In some embodiments, pattern matching may be probabilistic. For example, the system may determine with 70% confidence that the user was rowing, determine with 27% confidence that the user was using an elliptical, and determine with 3% confidence that the user was doing something that was unidentified. Thus, the pattern match may be based on a probability that the user is engaged in an activity rather than providing a one-to-one match. In an example, a set of probabilities may be calculated corresponding to the set of reference fingerprints, each probability of the set of probabilities may indicate a probability that a respective reference fingerprint matches the activity fingerprint. A reference fingerprint of the set of reference fingerprints having the highest probability of the set of probabilities may be selected as the closest matching reference fingerprint. A caloric expenditure may be calculated for the activity using a caloric expenditure corresponding to the selected reference fingerprint of the set of reference fingerprints.

The activity processing engine 120 may use the caloric expenditure corresponding to the selected reference activity to calculate a caloric expenditure for the time period. For example, the period of time may be thirty minutes and the selected reference activity may be running with a caloric expenditure of 15 calories per minute resulting in a total caloric expenditure for the period of time of 450 calories. The activity processing engine 120 may store (e.g., in a database, file, etc.) the total caloric expenditure for the time period. The activity processing engine 120 may generate a graphical user interface for output on a display of the portable device 115. The graphical user interface may include the total caloric expenditure. In addition, the graphical user interface may be continually updated to show a current caloric expenditure per minute corresponding to a currently selected reference activity.

In some examples, reference activity fingerprints may be created by placing the activity processing engine 120 in a training mode. For example, the user 105 may indicate via a graphical user interface of the portable device 115 that the user 105 is about to begin an activity. The user 105 may indicate via the graphical user interface that the activity has ended. The period of time may be determined as the period of time between the indication of the beginning of the activity and the indication of the end of the activity. Individual fingerprints may be created for each of the sensors and an aggregate activity fingerprint may be created as previously detailed. The activity fingerprint may be added to the set of reference activity fingerprints.

A caloric expenditure may be stored with the reference activity fingerprint. The caloric expenditure may be selected based on a label for the activity provided by the user 105. For example, the user 105 may select a label of running at a moderate pace as a label for the reference activity and the label may correspond to an estimated caloric expenditure of 15 calories per minute. In some examples, a graphical user interface may be generated that prompts the user 105 to answer a series of questions (e.g., heart rate, age, weight, etc.) and the caloric expenditure is based on a set of inputs received in response to the prompts. In some examples, the user 105 may be wearing a wearable fitness device which may be communicatively coupled to the activity processing engine 120. The activity processing engine 120 may evaluate inputs received from the wearable fitness device over the period of time to calculate an estimated caloric expenditure for the reference activity.

In some examples, each of the individual sensor fingerprints may be stored with the aggregate activity fingerprint. In some instances, a set of sensors used to create an activity fingerprint may vary for a set of sensors used to generate a reference activity fingerprint. For example, a reference activity fingerprint may include an audio fingerprint and a tablet used to generate the activity fingerprint may not have a working microphone. The activity processing engine 120 may use the stored individual fingerprints to generate a reference fingerprint that matches the sensor data received from the tablet. The activity processing engine 120 is discussed in more detail in FIG. 2.

While the environment 100 includes a piece of exercise equipment, it will be understood that the present subject matter may be used in instances where the user 105 is not using a piece of exercise equipment (e.g., doing pushups, jogging on a track or outdoors, etc.). The present subject matter is applicable to instances in which the portable device 115 is on the body of the user 105, on a piece of exercise equipment 110, and in the vicinity of the user and/or a piece of exercise equipment.

Figure 2:
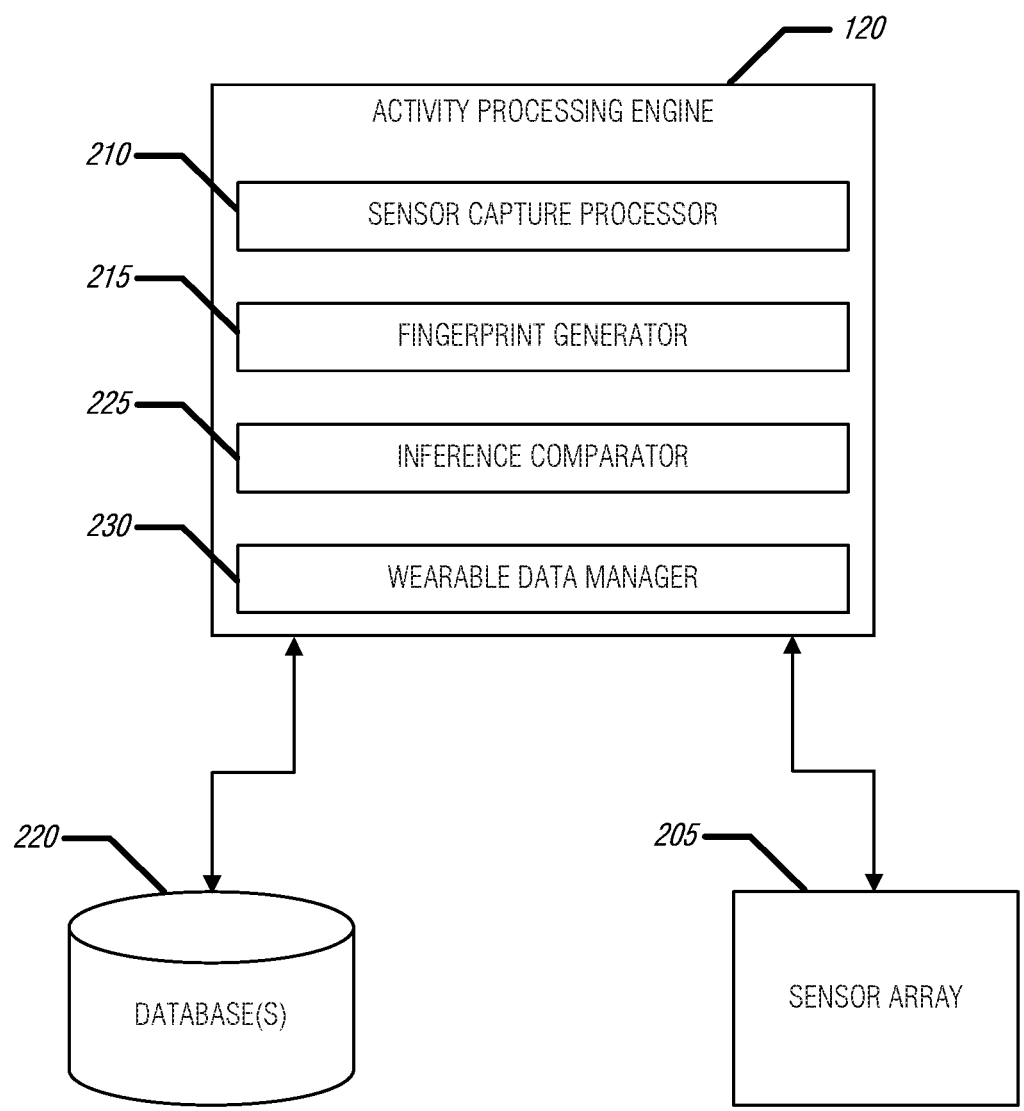
FIG. 2 illustrates a block diagram of an example of a system for tracking caloric expenditure using sensor driven fingerprints, according to an embodiment.

FIG. 2 illustrates a block diagram of an example of a system 200 for tracking caloric expenditure using sensor driven fingerprints, according to an embodiment. The system 200 may include an activity processing engine 120. The activity processing engine 120 may include a sensor capture processor 210, a fingerprint generator 215, an inference comparator 225, and a wearable data manager 230. The activity processing engine 120 may be communicatively coupled to one or more databases 220 and a sensor array 205.

The sensor array 205 may be a set of sensors included in a portable device such as, for example, a smartphone or tablet. The sensor array 205 may include a variety of sensors such as, for example, a microphone, a camera, an accelerometer, a gyroscope, a GPS receiver, a wireless transmitter, etc. The sensor array 205 may be placed in proximity to a user. The sensor array 205 may detect data about the user and an environment surrounding the user. For example, the sensor array 205 may be included in the user's smartphone which may be placed on a piece of exercise equipment such as a treadmill. The sensor array 205 may collect data within its range, for example, movement of the treadmill and the user, audio, video, location, etc.

The sensor capture processor 210 may collect the data from each sensor of the sensor array 205. For example, GPS location, a Wi-Fi signature (e.g., SSID information, signal strength, etc.), the existence of a paired wireless device, accelerometer data, gyroscope data, compass data, light, audio, and image output may be received from a plurality of sensors such as the sensor array 205. The sensor capture processor 210 may normalize the raw data or otherwise format the raw data for use by the activity processing engine 120. In an example, the sensor capture processor 210 may receive sensor data directly from each sensor. In an example, the sensor capture processor 210 may receive sensor data from another application (e.g., via an API, etc.).

The fingerprint generator 215 may generate a fingerprint for an activity using sensor data provided by the sensor capture processor 210. A fingerprint may be generated using the set of outputs received from the sensor array 205. The fingerprint may correspond to an activity observed by the plurality of sensors. For example, the user may be running on a treadmill and the fingerprint may be generated for the activity using sensor data such as vibration of the treadmill, location, audio, video, and light level. The fingerprint generator 215 may extract features (e.g., statistics, time domain, frequency domain, dimensionality reduction, etc.) for each of the sensors to characterize different aspects of the ongoing activity. Features from different sensors may then be merged together to form a fingerprint vector.

An example implementation may include plotting the vector in an n-dimensional space, where the dimensions correspond to components of the vector (e.g., an average jitter in location calculated from an accelerometer in a portable device sitting on the treadmill). As the components are assembled to create a plurality of vectors, the vectors may be compared against other user's vectors, or other vector collections corresponding to different user activities, to differentiate between users or activities based on the vectors. Thus, the collection of vectors for a given user serve as a fingerprint of the user, of a user activity, etc. This fingerprint, in this example implementation, is embodied by the vectors forming a model. Alternative model building from the component pieces may also occur, such as the training of a neural network with the components acting as inputs.

Thus, the fingerprint may encode information across all sensing modalities. Similarity of the sensor data may be estimated by pattern matching (e.g., Euclidian distance, cosine distance, KL divergence, etc.) between the fingerprint vectors. The fingerprint vector may be calculated on an appropriate time window corresponding to the activity.

In some embodiments, the fingerprint generator 215 may generate multiple fingerprints separated by time domain in order to model different activities. For example, an audio sensor may provide a different signature if the user is running on a treadmill vs. using a rowing machine in a gym. The user may use both machines in the same visit and may have different signatures divided by time.

In some examples, the window may be determined for each sensor in the sensor array 205 to accommodate for specific behavior of each sensor. For example, the placement of a portable device including the sensor array 205 may change throughout the activity. In such a case, a time window may be defined that is specifically applicable to the location sensor. In some examples, the user may be completing a variety of activities during a time window. In an example, the placement of a portable device may be calculated using accelerometer data, magnetometer data, audio, and video. Several fingerprints may be generated corresponding to each detected placement of the portable device.

The inference comparator 225 may compare an activity fingerprint generated by the fingerprint generator 215 to a set of reference fingerprints. In an example, the inference comparator 225 may be communicatively coupled to the one or more databases 220. The one or more databases 220 may store the set of reference fingerprints. Each reference fingerprint of the set of reference fingerprints may correspond to a caloric expenditure. In an example, the activity fingerprint may be compared to the set of reference fingerprints stored in the one or more databases 220.

Different sensors of the sensor array 205 may play different roles in fingerprinting. For example, GPS data, wireless communication data, video, and audio may be used to obtain more accurate localization in the environment while accelerometer data and audio may be used to distinguish whether the user is actually using a treadmill (e.g., whether the treadmill is running vs. whether the user is standing next to the treadmill talking with a friend, etc.).

The behavior of the inference comparator 225 may vary based on whether data is available from a wearable fitness device. If data is available from the wearable fitness device, the inference comparator 225 may request activity data and caloric expenditure data from the wearable fitness device. The activity data and caloric expenditure data may then be associated with the activity fingerprint. If the inference comparator 225 is unable to match the activity fingerprint to a reference fingerprint of the set of reference fingerprints the activity fingerprint may be added to the set of reference fingerprints and associated with the caloric expenditure data received from the wearable fitness device. If the activity fingerprint matches a reference fingerprint of the set of reference fingerprints, the matching reference fingerprint may be updated to reflect the activity data and caloric expenditure data received from the wearable fitness device resulting in increased accuracy of the matched reference fingerprint for future use.

If data is not available from a wearable fitness device, the inference comparator 225 may use past data to infer the user's exercise profile (e.g., activity, intensity, and caloric expenditure). The inference comparator may use pattern matching techniques to compare the activity fingerprint to the set of reference fingerprints. When a matching fingerprint is found the inference comparator 225 may use a caloric expenditure corresponding to the matching reference fingerprint to calculate a caloric expenditure for the activity. The calculation may use a caloric expenditure per minute corresponding to the reference fingerprint and the time window to calculate a total caloric expenditure for the activity. In some examples, the activity processing engine 120 may maintain an exercise profile for the user and the exercise profile may be updated using the calculated caloric expenditure.

In some examples, a hardware implemented pattern-matching accelerator may be employed. The hardware implemented pattern-matching accelerator may be programmed to evaluate sensor inputs using a pattern-matching technique for real-time or near real-time matching of an activity fingerprint to a reference fingerprint. The hardware implemented pattern-matching accelerator may be communicatively coupled to the one or more databases 220 (e.g., via network, circuitry, etc.).

The wearable data manager 230 may collect activity data and caloric expenditure data from the wearable fitness device. For example, the user may be wearing a fitness tracking watch and the wearable data manager 230 may collect activity data and caloric expenditure data output by the fitness tracking watch. In an example, the wearable data manager 230 may collect the activity data and the caloric expenditure data directly from the wearable fitness device (e.g., via wireless connection, operating system service, etc.). In an example, the wearable data manager 230 may collect the activity data and the caloric expenditure data from an application associated with the wearable fitness device (e.g., via API call, etc.).

In some examples, the activity processing engine 120 may be communicatively coupled to a network service (e.g., cloud based service, etc.). In some examples, reference fingerprints may be generated using individual or aggregated data submitted by other users and stored by the network service. In an example, if the activity fingerprint does not match a reference fingerprint in the one or more databases 220 the inference comparator 225 may compare the activity fingerprint to a set of server-based reference fingerprints. Each of the server-based fingerprints may be statistically associated with a caloric expenditure. For example, the user may be jogging outside and a matching reference fingerprint was not found. A server-based reference fingerprint may be matched to the activity and the server-based fingerprint may be determined to be statistically similar to a local reference fingerprint for running on a treadmill. As a result, the caloric expenditure corresponding to running on a treadmill may be selected and used to calculate the caloric expenditure of the activity. In an example, the user may upload an activity fingerprint to the network service. In an example, another user may compare a second activity fingerprint to the uploaded activity fingerprint.

In some examples, the user may associate an activity fingerprint with a piece of fitness equipment and the inference comparator may calculate a caloric expenditure using a typical caloric expenditure for the piece of fitness equipment. For example, the user may run on a treadmill that may have a typical caloric expenditure of 16 calories per minute. The user may associate the activity fingerprint with the treadmill and the caloric expenditure may be calculated using the typical caloric expenditure of 16 calories per minute. In an example, the user may be able to input demographic data (e.g., age, weight, etc.) into a graphical user interface provided by the activity processing engine 120 and the inference comparator 225 may adjust the caloric expenditure using the demographic data.

In some examples, the inference comparator 225 may collect context data (e.g., day of the week, weather, user routines, etc.) to better estimate caloric expenditure. For example, the activity processing engine 120 may determine differences in treadmill use based on context such as the user runs hills on Fridays, flatter surfaces on Mondays, and intervals on Wednesdays. For example, if a user is not wearing their usual fitness tracker, but does have their phone with them at the gym, the sensors from the phone may recognize that the user is likely to be on the treadmill due to the sound profile of the treadmill, the electromagnetic signature of the treadmill, the local triangulation of WiFi, the repeated sound of foot stomps, or a characteristic accelerometer reading from foot impacts on the treadmill that impact the machine on which the phone may normally rest. Combining the sensor data and the time of day and day of the week, a fingerprint may be formed that may be matched to a model of the user's behavior and a best match may be found with the treadmill "Running Hills" activity as it may be the users' habit to run hills on Fridays on the treadmill and an estimate of caloric expenditure passed on the mean value of caloric expenditure from prior Friday "Running Hills" sessions may be substituted as proxy data for the current time domain. Similarly it may be the user's habit to participate in a Step Aerobics class on Tuesday mornings, and a fingerprint consisting of a GPS Location, a WiFi triangulation, and an audio signature of songs usually played during Step Aerobics may match current sensor data, the mean calorie expenditure from prior Step Aerobics classes of this type may be substituted for the current time domain.

The inference comparator 225 may use the context information to adjust the caloric expenditure resulting in more accurate estimates. In some examples, the proximity of other users' devices may be used by the inference comparator 225 to adjust the caloric expenditure for an activity. For example, it may be determined that caloric expenditure of the user rises when friends portable devices are within proximity and the caloric expenditure may be adjusted upwards as a result.

In some examples, received inputs from additional data sources may be used in calculating caloric expenditure. For example, the user may establish a connection (e.g., by subscribing to a data stream, could-based services, etc.) between a smartphone and a sensor augmented exercise machine. The addition data sources may contain activity data and context data that may be used by the inference comparator 225 to adjust the caloric expenditure. For example, a weigh machine may provide weight and repetition information that may be used in calculating the caloric expenditure.

Figure 5:
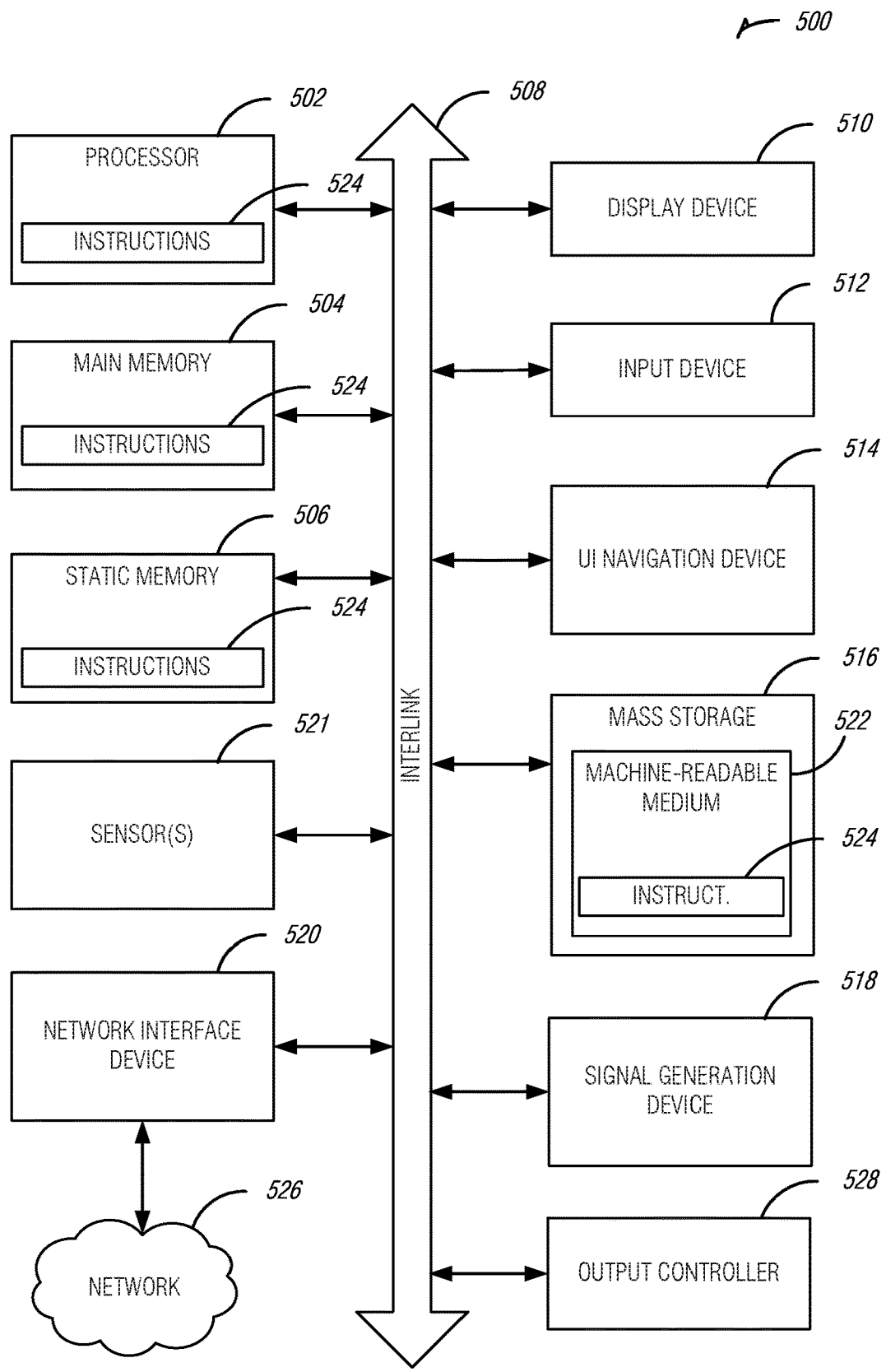
FIG. 5 is a block diagram illustrating an example of a machine upon which one or more embodiments may be implemented.

The activity processing engine 120, sensor capture processor 210, fingerprint generator 215, inference comparator 225, and wearable data manager 230 may comprise one or more processors (e.g., hardware processor 502 described in FIG. 5, etc.) that execute software instructions, such as those used to define a software or computer program, stored in a computer-readable storage medium such as a memory device (e.g., a main memory 504 and a static memory 506 as described in FIG. 5, a Flash memory, random access memory (RAM), or any other type of volatile or non-volatile memory that stores instructions), or a storage device (e.g., a disk drive, or an optical drive). Alternatively, the activity processing engine 120, sensor capture processor 210, fingerprint generator 215, inference comparator 225, and wearable data manager 230 may comprise dedicated hardware, such as one or more integrated circuits, one or more Application Specific Integrated Circuits (ASICs), one or more Application Specific Special Processors (ASSPs), one or more Field Programmable Gate Arrays (FPGAs), or any combination of the foregoing examples of dedicated hardware, for performing the techniques described in this disclosure.

Figure 3:
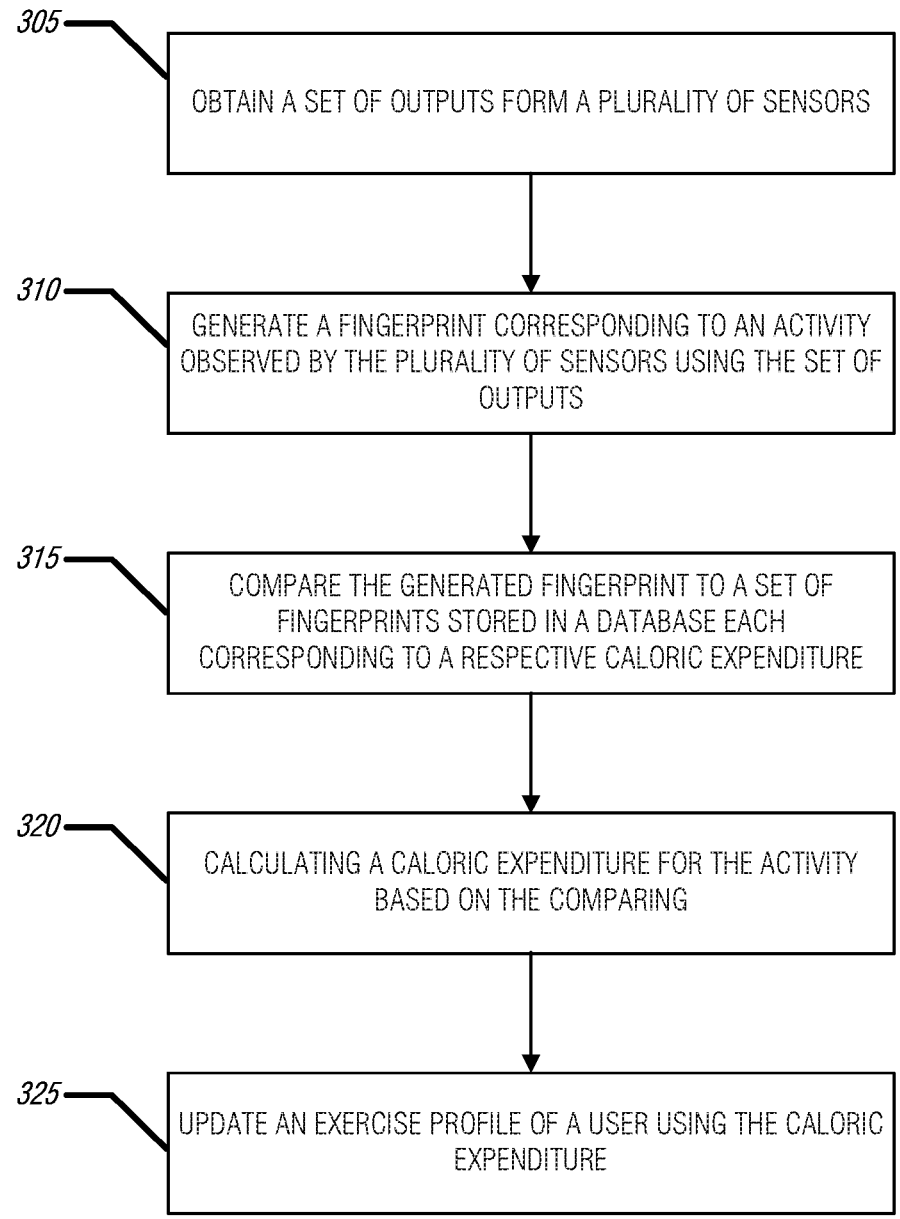
FIG. 3 illustrates a flow diagram of an example of a method for tracking caloric expenditure using sensor driven fingerprints, according to an embodiment.

FIG. 3 illustrates a flow diagram of an example of a method 300 for tracking caloric expenditure using sensor driven fingerprints, according to an embodiment. The method 300 may provide similar functionality as described in FIGS. 1 & 2 above.

At operation 305, a set of sensor outputs may be obtained from a plurality of sensors. In an example, the plurality of sensors may include at least one of an accelerometer, a gyroscope, a compass, a global positioning receiver, a light sensor, a microphone, and a camera. In an example, the plurality of sensors may be embedded in a smartphone device. In an example, the plurality of sensors may be embedded in a wearable device. In an example, the plurality of sensors may be included in a portable device.

At operation 310, a fingerprint may be generated using the set of outputs. The fingerprint may correspond to an activity observed by the plurality of sensors. For example, a user may be running on a treadmill and the fingerprint may correspond to the user running on the treadmill. In an example, features may be extracted for each sensor of the plurality of sensors included in the set of outputs to form a fingerprint vector for each sensor of the plurality of sensors over a period of time. The fingerprint vector for each sensor may be merged to form an aggregate fingerprint vector for the period of time. The fingerprint may be generated using the aggregate fingerprint vector. In an example, merging the fingerprint vector for each sensor may include using pattern matching to find a similarity between a first feature extracted from a first sensor of the plurality of sensors and a second feature extracted from a second sensor of the plurality of sensors.

At operation 315, the generated fingerprint may be compared to a set of fingerprints stored in a database. Each fingerprint of the set of fingerprints may correspond to a respective caloric expenditure.

At operation 320, a caloric expenditure may be calculated for the activity based on the comparison. In an example, a context associated with the activity may be received and the caloric expenditure may be adjusted based on the context. For example, the user may run harder on a treadmill on Mondays and the context received may be that the user is running on the treadmill on a Monday and the caloric expenditure may be adjusted upwards. In an example, user attributes may be obtained from an exercise profile of the user and the caloric expenditure may be adjusted using the user attributes. For example, the user may have a gender attribute of female, an age attribute of 28 and a weight attribute of 160 pounds and the caloric expenditure may be adjusted by applying an adjustment coefficient determined for a 160 pound, 28 year old, female. In an example, a set of data may be received from a smart exercise device and the caloric expenditure may be adjusted using the set of data. For example, the set of data may include a weight being lifted and a number of repetitions and the caloric expenditure may be adjusted using the weight and repletion data.

At operation 325, an exercise profile of a user may be updated using the caloric expenditure. For example, the exercise profile of the user may contain a record of activities, fingerprints, and caloric expenditures. The record may be appended with the calculated caloric expenditure. In some example, the fingerprint may be stored in a database corresponding to the user. In an example, the fingerprint vector for each sensor of the plurality of sensors may be stored in the database corresponding to the user. In an example, the aggregate fingerprint may be uploaded to network based service.

In some examples, a training mode graphical user interface may be provided on a mobile device. A set of outputs may be received from at least one sensor in a wearable device. An indication may be obtained via the training mode graphical user interface that an activity has commenced. A training fingerprint may be generated for the set of outputs. The training fingerprint may be stored in the database.

Figure 4:
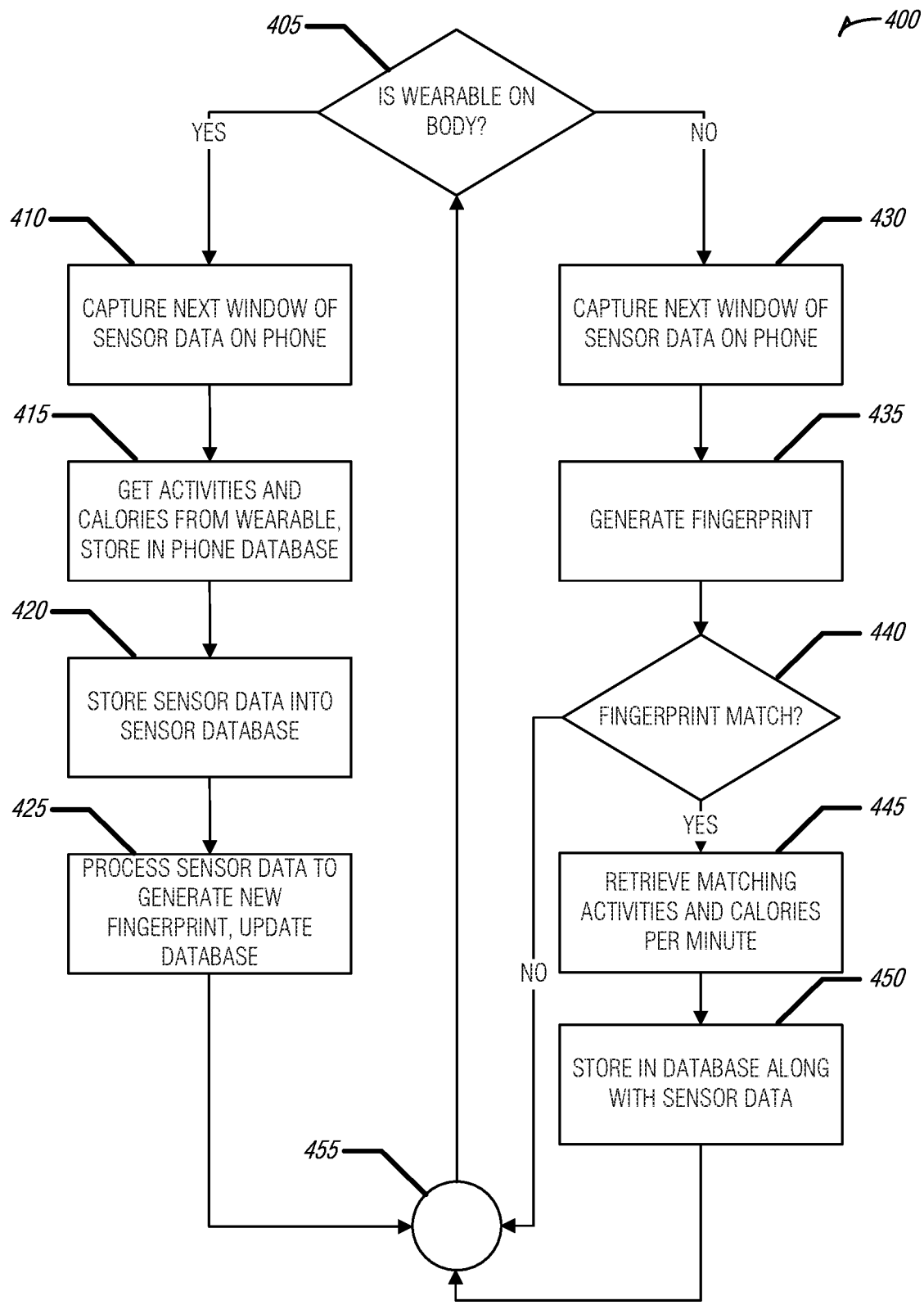
FIG. 4 illustrates a flow diagram of an example of a method for tracking caloric expenditure using sensor driven fingerprints, according to an embodiment.

FIG. 4 illustrates a flow diagram of an example of a method 400 for tracking caloric expenditure using sensor driven fingerprints, according to an embodiment. The method 400 may include similar functionality as described in FIGS. 1-3.

At decision 405, it may be determined (e.g., is data available, is a connection detected, etc.) if a user is wearing a wearable fitness device (e.g., a personal fitness tracker, fitness watch, etc.). If the user is wearing a wearable fitness device processing continues at operation 410. At operation 410, a next window of sensor data may be captured from a smartphone. In an example, a start point and an end point may be determined for a time window for sensor data collection. In an example, the start point and end point may be determined based on the detection of a change in sensor data collected from an array of sensors. At operation 415, activities and caloric expenditure may be obtained from the wearable fitness device and may be stored in a database on the smartphone. For example, the wearable fitness device may produce output consisting of activity data and caloric expenditure data that may be retrieved directly from the device and/or via an API call to an application associated with the wearable fitness device.

At operation 420 sensor data may be stored into a sensor database. For example, sensor data (e.g., audio, video, movement data, etc.) collected from a sensor array included in the smartphone may be stored in the sensor database. The sensor database may be located on the smartphone. In some examples, the smartphone may be communicatively coupled to a network database server. At operation 425, the sensor data may be processed to generate a new fingerprint and the database in updated. For example, acceleration data, audio, and video collected from the sensor array may be processed to create a fingerprint that is stored in a fingerprint database on the smartphone. In an example, the fingerprint may be added to a set of reference fingerprints included in the database. At 455 the method 400 returns to decision 405 for processing a subsequent window of sensor data.

If the user is not determined to be wearing a wearable fitness device on their body at decision 405, processing continues to process 430. At process 430, a next window of sensor data may be captured from a smartphone. In an example, a start point and an end point may be determined for a time window for sensor data collection. In an example, the start point and end point may be determined based on the detection of a change in sensor data collected from an array of sensors. At process 435, a fingerprint is generated from the captured sensor data. For example, accelerometer data, location date, audio, and video collected from the array of sensors may be aggregated to generate an activity fingerprint for the window of time. At decision 440, it is determined if the fingerprint matches a reference fingerprint stored in the database. If a matching reference fingerprint the process may end at 455 and begin again at decision 405.

If a matching reference fingerprint is found at decision 440, processing continues to operation 445. At operation 445, matching activities and caloric expenditure per minute are retrieved. For example, the user may be running on a treadmill and the activity fingerprint generated for the time window may be matched to reference activity of a previous running session on the treadmill. The activity and the caloric expenditure may be retrieved and used to calculate a caloric expenditure for the time window. At operation 450, the activities, calories per minute, and sensor data may be stored in the database. In an example, the sensor data may be used to update the matched reference fingerprint for more accurate future matching.

FIG. 5 illustrates a block diagram of an example machine 500 upon which any one or more of the techniques (e.g., methodologies) discussed herein may perform. In alternative embodiments, the machine 500 may operate as a standalone device or may be connected (e.g., networked) to other machines. In a networked deployment, the machine 500 may operate in the capacity of a server machine, a client machine, or both in server-client network environments. In an example, the machine 500 may act as a peer machine in peer-to-peer (P2P) (or other distributed) network environment. The machine 500 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 500 may include a hardware processor 502 (e.g., a central processing unit (CPU), a graphics processing unit (GPU), a hardware processor core, or any combination thereof), a main memory 504 and a static memory 506, some or all of which may communicate with each other via an interlink (e.g., bus) 508. The machine 500 may further include a display unit 510, an alphanumeric input device 512 (e.g., a keyboard), and a user interface (UI) navigation device 514 (e.g., a mouse). In an example, the display unit 510, input device 512 and UI navigation device 514 may be a touch screen display. The machine 500 may additionally include a storage device (e.g., drive unit) 516, a signal generation device 518 (e.g., a speaker), a network interface device 520, and one or more sensors 521, such as a global positioning system (GPS)

sensor, compass, accelerometer, or other sensor. The machine 500 may include an output controller 528, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 516 may include a machine readable medium 522 on which is stored one or more sets of data structures or instructions 524 (e.g., software) embodying or utilized by any one or more of the techniques or functions described herein. The instructions 524 may also reside, completely or at least partially, within the main memory 504, within static memory 506, or within the hardware processor 502 during execution thereof by the machine 500. In an example, one or any combination of the hardware processor 502, the main memory 504, the static memory 506, or the storage device 516 may constitute machine readable media.

While the machine readable medium 522 is illustrated as a single medium, the term "machine readable medium" may include a single medium or multiple media (e.g., a centralized or distributed database, and/or associated caches and servers) configured to store the one or more instructions 524.

The term "machine readable medium" may include any medium that is capable of storing, encoding, or carrying instructions for execution by the machine 500 and that cause the machine 500 to perform any one or more of the techniques of the present disclosure, or that is capable of storing, encoding or carrying data structures used by or associated with such instructions. Non-limiting machine readable medium examples may include solid-state memories, and optical and magnetic media. In an example, a massed machine readable medium comprises a machine readable medium with a plurality of particles having invariant (e.g., rest) mass. Accordingly, massed machine-readable media are not transitory propagating signals. Specific examples of massed machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 524 may further be transmitted or received over a communications network 526 using a transmission medium via the network interface device 520 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 520 may include one or more physical jacks (e.g., Ethernet, coaxial, or phone jacks) or one or more antennas to connect to the communications network 526. In an example, the network interface device 520 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 500, and includes digital or analog communications signals or other intangible medium to facilitate communication of such software.

ADDITIONAL NOTES & EXAMPLES

Example 1 is a system for tracking caloric expenditure using sensor driven fingerprints, the system comprising: a sensor capture processor to obtain a set of outputs from a plurality of sensors; a fingerprint generator to generate a fingerprint using the set of outputs, the fingerprint corresponding to an activity observed by the plurality of sensors; and an inference comparator to: compare the generated fingerprint to a set of fingerprints stored in a database, each fingerprint of the set of fingerprints corresponding to a respective caloric expenditure; calculate a caloric expenditure for the activity based on the comparison; and update an exercise profile of a user using the caloric expenditure.

In Example 2, the subject matter of Example 1 optionally includes the inference comparator further to: identify that the generated fingerprint does not match a fingerprint of the set of fingerprints; determine a caloric expenditure corresponding to the generated finger print; and store, in the database, the generated fingerprint and the corresponding calculated caloric expenditure.

In Example 3, the subject matter of any one or more of Examples 1-2 optionally include wherein the plurality of sensors includes at least one of an accelerometer, gyroscope, compass, global positioning receiver, light sensor, microphone, and camera.

In Example 4, the subject matter of any one or more of Examples 1-3 optionally include fingerprint generator further to: extract features from each sensor of the plurality of sensors included in the set of outputs to generate a fingerprint vector for each sensor of the plurality of sensors over a time period; and merge the fingerprint vector for each sensor to form an aggregate fingerprint vector for the time period; and generate the fingerprint using the aggregate fingerprint vector.

In Example 5, the subject matter of Example 4 optionally includes the fingerprint generator further to use pattern matching to find a similarity between a first feature extracted from a first sensor of the plurality of sensors and a second feature extracted from a second sensor of the plurality of sensors.

In Example 6, the subject matter of any one or more of Examples 1-5 optionally include the inference comparator further to: receive a context associated with the activity; and adjust the caloric expenditure based on the context.

In Example 7, the subject matter of any one or more of Examples 1-6 optionally include the inference comparator further to: obtain user attributes from the exercise profile of the user; and adjust the caloric expenditure using the user attributes.

In Example 8, the subject matter of any one or more of Examples 1-7 optionally include wherein the plurality of sensors are embedded in a smartphone device.

In Example 9, the subject matter of Example 8 optionally includes wherein the smartphone device conforms to a 3GPP LTE standard.

In Example 10, the subject matter of any one or more of Examples 1-9 optionally include wherein the plurality of sensors includes at least one sensor embedded in a wearable device.

In Example 11, the subject matter of any one or more of Examples 1-10 optionally include wherein the set of inputs is obtained over short-wavelength radio.

In Example 12, the subject matter of any one or more of Examples 1-11 optionally include the inference comparator further to: receive a set of data from a smart exercise device; and adjust the caloric expenditure using the set of data.

In Example 13, the subject matter of any one or more of Examples 1-12 optionally include an activity processing engine to: provide a training mode graphical user interface on a mobile device; obtain an indication, via the training mode graphical user interface, that an activity has commenced; and wherein the sensor capture processor is further to receive a set of outputs from at least one sensor in a wearable device, and wherein the fingerprint generator is further to generate a training fingerprint for the set of outputs and store the training fingerprint in the database.

In Example 14, the subject matter of any one or more of Examples 1-13 optionally include the inference comparator further to: calculate a set of probabilities corresponding to the set of fingerprints, each probability of the set of probabilities indicating a probability that a respective fingerprint matches the generated fingerprint; and select a fingerprint of the set of fingerprints having the highest probability of the set of probabilities; wherein the inference comparator uses a caloric expenditure corresponding to the selected fingerprint of the set of fingerprints to calculate the caloric expenditure for the activity.

Example 15 is a system for tracking caloric expenditure using sensor driven fingerprints, the system comprising: means for obtaining a set of outputs from a plurality of sensors; means for generating a fingerprint using the set of outputs, the fingerprint corresponding to an activity observed by the plurality of sensors; means for comparing the generated fingerprint to a set of fingerprints stored in a database, each fingerprint of the set of fingerprints corresponding to a respective caloric expenditure; means for calculating a caloric expenditure for the activity based on the comparing; and means for updating an exercise profile of a user using the caloric expenditure.

In Example 16, the subject matter of Example 15 optionally includes means for identifying that the generated fingerprint does not match a fingerprint of the set of fingerprints; means for determining a caloric expenditure corresponding to the generated finger print; and means for storing the generated fingerprint and the corresponding calculated caloric expenditure.

In Example 17, the subject matter of any one or more of Examples 15-16 optionally include wherein the plurality of sensors includes at least one of an accelerometer, gyroscope, compass, global positioning receiver, light sensor, microphone, and camera.

In Example 18, the subject matter of any one or more of Examples 15-17 optionally include means for extracting features from each sensor of the plurality of sensors included in the set of outputs to generate a fingerprint vector for each sensor of the plurality of sensors over a time period; and means for merging the fingerprint vector for each sensor to form an aggregate fingerprint vector for the time period; and means for generating the fingerprint using the aggregate fingerprint vector.

In Example 19, the subject matter of Example 18 optionally includes means for using pattern matching to find a similarity between a first feature extracted from a first sensor of the plurality of sensors and a second feature extracted from a second sensor of the plurality of sensors.

In Example 20, the subject matter of any one or more of Examples 15-19 optionally include means for receiving a context associated with the activity; and means for adjusting the caloric expenditure based on the context.

In Example 21, the subject matter of any one or more of Examples 15-20 optionally include means for obtaining user attributes from the exercise profile of the user; and means for adjusting the caloric expenditure using the user attributes.

In Example 22, the subject matter of any one or more of Examples 15-21 optionally include wherein the plurality of sensors are embedded in a smartphone device.

In Example 23, the subject matter of Example 22 optionally includes wherein the smartphone device conforms to a 3GPP LTE standard.

In Example 24, the subject matter of any one or more of Examples 15-23 optionally include wherein the plurality of sensors includes at least one sensor embedded in a wearable device.

In Example 25, the subject matter of any one or more of Examples 15-24 optionally include wherein the means for obtaining the set of inputs from the plurality of sensors includes means for obtaining the set of inputs over short-wavelength radio.

In Example 26, the subject matter of any one or more of Examples 15-25 optionally include means for receiving a set of data from a smart exercise device; and means for adjusting the caloric expenditure using the set of data.

In Example 27, the subject matter of any one or more of Examples 15-26 optionally include means for providing a training mode graphical user interface on a mobile device; means for receiving a set of outputs from at least one sensor in a wearable device; means for obtaining an indication, via the training mode graphical user interface, that an activity has commenced; means for generating a training fingerprint for the set of outputs; and means for storing the training fingerprint in the database.

In Example 28, the subject matter of any one or more of Examples 15-27 optionally include means for calculating a set of probabilities corresponding to the set of fingerprints, each probability of the set of probabilities indicating a probability that a respective fingerprint matches the generated fingerprint; and means for selecting a fingerprint of the set of fingerprints having the highest probability of the set of probabilities; wherein the means to calculate the caloric expenditure for the activity includes means for using a caloric expenditure corresponding to the selected fingerprint of the set of fingerprints.

Example 29 is a system for tracking caloric expenditure using sensor driven fingerprints, the system comprising: at least one processor; and at least one machine readable memory including instructions that, when executed by the at least one processor, cause the at least one processor to: obtain a set of outputs from a plurality of sensors; generate a fingerprint using the set of outputs, the fingerprint corresponding to an activity observed by the plurality of sensors; compare the generated fingerprint to a set of fingerprints stored in a database, each fingerprint of the set of fingerprints corresponding to a respective caloric expenditure; calculate a caloric expenditure for the activity based on the comparison; and update an exercise profile of a user using the caloric expenditure.

In Example 30, the subject matter of Example 29 optionally includes wherein the instructions to compare the generated fingerprint to the set of fingerprints and calculate the caloric expenditure includes instructions to: identify that the generated fingerprint does not match a fingerprint of the set of fingerprints; determine a caloric expenditure corresponding to the generated finger print; and store, in the database, the generated fingerprint and the corresponding calculated caloric expenditure.

In Example 31, the subject matter of any one or more of Examples 29-30 optionally include wherein the plurality of sensors includes at least one of an accelerometer, gyroscope, compass, global positioning receiver, light sensor, microphone, and camera.

In Example 32, the subject matter of any one or more of Examples 29-31 optionally include wherein the instructions to generate the fingerprint includes instructions to: extract features from each sensor of the plurality of sensors included in the set of outputs to generate a fingerprint vector for each sensor of the plurality of sensors over a time period; and merge the fingerprint vector for each sensor to form an aggregate fingerprint vector for the time period; and generate the fingerprint using the aggregate fingerprint vector.

In Example 33, the subject matter of Example 32 optionally includes wherein the instructions to merge the fingerprint vector for each sensor includes instructions to use pattern matching to find a similarity between a first feature extracted from a first sensor of the plurality of sensors and a second feature extracted from a second sensor of the plurality of sensors.

In Example 34, the subject matter of any one or more of Examples 29-33 optionally include instructions to: receive a context associated with the activity; and adjust the caloric expenditure based on the context.

In Example 35, the subject matter of any one or more of Examples 29-34 optionally include instructions to: obtain user attributes from the exercise profile of the user; and adjust the caloric expenditure using the user attributes.

In Example 36, the subject matter of any one or more of Examples 29-35 optionally include wherein the plurality of sensors are embedded in a smartphone device.

In Example 37, the subject matter of Example 36 optionally includes wherein the smartphone device conforms to a 3GPP LTE standard.

In Example 38, the subject matter of any one or more of Examples 29-37 optionally include wherein the plurality of sensors includes at least one sensor embedded in a wearable device.

In Example 39, the subject matter of any one or more of Examples 29-38 optionally include wherein the set of inputs is obtained over short-wavelength radio.

In Example 40, the subject matter of any one or more of Examples 29-39 optionally include instructions to: receive a set of data from a smart exercise device; and adjust the caloric expenditure using the set of data.

In Example 41, the subject matter of any one or more of Examples 29-40 optionally include instructions to: provide a training mode graphical user interface on a mobile device; receive a set of outputs from at least one sensor in a wearable device; obtain an indication, via the training mode graphical user interface, that an activity has commenced; generate a training fingerprint for the set of outputs; and store the training fingerprint in the database.

In Example 42, the subject matter of any one or more of Examples 29-41 optionally include wherein the instructions to compare the generated fingerprint to the set of fingerprints stored in the database includes instructions to: calculate a set of probabilities corresponding to the set of fingerprints, each probability of the set of probabilities indicating a probability that a respective fingerprint matches the generated fingerprint; and select a fingerprint of the set of fingerprints having the highest probability of the set of probabilities; wherein the instructions to calculate the caloric expenditure for the activity includes instructions to use a caloric expenditure corresponding to the selected fingerprint of the set of fingerprints.

Example 43 is a method for tracking caloric expenditure using sensor driven fingerprints, the method comprising: obtaining a set of outputs from a plurality of sensors; generating, using at least one processor, a fingerprint using the set of outputs, the fingerprint corresponding to an activity observed by the plurality of sensors; comparing, using at least one processor, the generated fingerprint to a set of fingerprints stored in a database, each fingerprint of the set of fingerprints corresponding to a respective caloric expenditure; calculating, using at least one processor, a caloric expenditure for the activity based on the comparing; and updating an exercise profile of a user using the caloric expenditure.

In Example 44, the subject matter of Example 43 optionally includes wherein comparing the generated fingerprint to the set of fingerprints includes: identifying that the generated fingerprint does not match a fingerprint of the set of fingerprints; determining a caloric expenditure corresponding to the generated finger print; and storing, in the database, the generated fingerprint and the corresponding calculated caloric expenditure.

In Example 45, the subject matter of any one or more of Examples 43-44 optionally include wherein the plurality of sensors includes at least one of an accelerometer, gyroscope, compass, global positioning receiver, light sensor, microphone, and camera.

In Example 46, the subject matter of any one or more of Examples 43-45 optionally include wherein generating the fingerprint includes: extracting features from each sensor of the plurality of sensors included in the set of outputs to generate a fingerprint vector for each sensor of the plurality of sensors over a time period; and merging the fingerprint vector for each sensor to form an aggregate fingerprint vector for the time period; and generating the fingerprint using the aggregate fingerprint vector.

In Example 47, the subject matter of Example 46 optionally includes wherein merging the fingerprint vector for each sensor includes using pattern matching to find a similarity between a first feature extracted from a first sensor of the plurality of sensors and a second feature extracted from a second sensor of the plurality of sensors.

In Example 48, the subject matter of any one or more of Examples 43-47 optionally include receiving a context associated with the activity; and adjusting the caloric expenditure based on the context.

In Example 49, the subject matter of any one or more of Examples 43-48 optionally include obtaining user attributes from the exercise profile of the user; and adjusting the caloric expenditure using the user attributes.

In Example 50, the subject matter of any one or more of Examples 43-49 optionally include wherein the plurality of sensors are embedded in a smartphone device.

In Example 51, the subject matter of Example 50 optionally includes wherein the smartphone device conforms to a 3GPP LTE standard.

In Example 52, the subject matter of any one or more of Examples 43-51 optionally include wherein the plurality of sensors includes at least one sensor embedded in a wearable device.

In Example 53, the subject matter of any one or more of Examples 43-52 optionally include wherein obtaining the set of inputs from the plurality of sensors includes obtaining the set of inputs over short-wavelength radio.

In Example 54, the subject matter of any one or more of Examples 43-53 optionally include receiving a set of data from a smart exercise device; and adjusting the caloric expenditure using the set of data.

In Example 55, the subject matter of any one or more of Examples 43-54 optionally include providing a training mode graphical user interface on a mobile device; receiving a set of outputs from at least one sensor in a wearable device; obtaining an indication, via the training mode graphical user interface, that an activity has commenced; generating a training fingerprint for the set of outputs; and storing the training fingerprint in the database.

In Example 56, the subject matter of any one or more of Examples 43-55 optionally include wherein comparing the generated fingerprint to the set of fingerprints stored in a database further comprises: calculating a set of probabilities corresponding to the set of fingerprints, each probability of the set of probabilities indicating a probability that a respective fingerprint matches the generated fingerprint; and selecting a fingerprint of the set of fingerprints having the highest probability of the set of probabilities; wherein calculating the caloric expenditure for the activity includes using a caloric expenditure corresponding to the selected fingerprint of the set of fingerprints.

Example 57 is a system for tracking caloric expenditure using sensor driven fingerprints, the system comprising means to perform any method of Examples 43-56.

Example 58 is a machine readable medium for tracking caloric expenditure using sensor driven fingerprints, the machine readable medium including instructions that, when executed by a machine, cause the machine to perform any method of Examples 43-56.

Example 59 is at least one machine readable medium including instructions for tracking caloric expenditure using sensor driven fingerprints that, when executed by at least one processor, cause the machine to: obtain a set of outputs from a plurality of sensors; generate a fingerprint using the set of outputs, the fingerprint corresponding to an activity observed by the plurality of sensors; compare the generated fingerprint to a set of fingerprints stored in a database, each fingerprint of the set of fingerprints corresponding to a respective caloric expenditure; calculate a caloric expenditure for the activity based on the comparison; and update an exercise profile of a user using the caloric expenditure.

In Example 60, the subject matter of Example 59 optionally includes wherein the instructions to compare the generated fingerprint to the set of fingerprints and calculate the caloric expenditure includes instructions to: identify that the generated fingerprint does not match a fingerprint of the set of fingerprints; determine a caloric expenditure corresponding to the generated finger print; and store, in the database, the generated fingerprint and the corresponding calculated caloric expenditure.

In Example 61, the subject matter of any one or more of Examples 59-60 optionally include wherein the plurality of sensors includes at least one of an accelerometer, gyroscope, compass, global positioning receiver, light sensor, microphone, and camera.

In Example 62, the subject matter of any one or more of Examples 59-61 optionally include wherein the instructions to generate the fingerprint includes instructions to: extract features from each sensor of the plurality of sensors included in the set of outputs to generate a fingerprint vector for each sensor of the plurality of sensors over a time period; and merge the fingerprint vector for each sensor to form an aggregate fingerprint vector for the time period; and generate the fingerprint using the aggregate fingerprint vector.

In Example 63, the subject matter of Example 62 optionally includes wherein the instructions to merge the fingerprint vector for each sensor includes instructions to use pattern matching to find a similarity between a first feature extracted from a first sensor of the plurality of sensors and a second feature extracted from a second sensor of the plurality of sensors.

In Example 64, the subject matter of any one or more of Examples 59-63 optionally include instructions to: receive a context associated with the activity; and adjust the caloric expenditure based on the context.

In Example 65, the subject matter of any one or more of Examples 59-64 optionally include instructions to: obtain user attributes from the exercise profile of the user; and adjust the caloric expenditure using the user attributes.

In Example 66, the subject matter of any one or more of Examples 59-65 optionally include wherein the plurality of sensors are embedded in a smartphone device.

In Example 67, the subject matter of Example 66 optionally includes wherein the smartphone device conforms to a 3GPP LTE standard.

In Example 68, the subject matter of any one or more of Examples 59-67 optionally include wherein the plurality of sensors includes at least one sensor embedded in a wearable device.

In Example 69, the subject matter of any one or more of Examples 59-68 optionally include wherein the set of inputs is obtained over short-wavelength radio.

In Example 70, the subject matter of any one or more of Examples 59-69 optionally include instructions to: receive a set of data from a smart exercise device; and adjust the caloric expenditure using the set of data.

In Example 71, the subject matter of any one or more of Examples 59-70 optionally include instructions to: provide a training mode graphical user interface on a mobile device; receive a set of outputs from at least one sensor in a wearable device; obtain an indication, via the training mode graphical user interface, that an activity has commenced; generate a training fingerprint for the set of outputs; and store the training fingerprint in the database.

In Example 72, the subject matter of any one or more of Examples 59-71 optionally include wherein the instructions to compare the generated fingerprint to the set of fingerprints stored in the database includes instructions to: calculate a set of probabilities corresponding to the set of fingerprints, each probability of the set of probabilities indicating a probability that a respective fingerprint matches the generated fingerprint; and select a fingerprint of the set of fingerprints having the highest probability of the set of probabilities; wherein the instructions to calculate the caloric expenditure for the activity includes instructions to use a caloric expenditure corresponding to the selected fingerprint of the set of fingerprints.

The above detailed description includes references to the accompanying drawings, which form a part of the detailed description. The drawings show, by way of illustration, specific embodiments that may be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is to allow the reader to quickly ascertain the nature of the technical disclosure and is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the embodiments should be determined with reference to the appended claims, along with the full scope of equivalents to which such claims are entitled.

What is claimed is:

1. A system for tracking caloric expenditure using sensor driven fingerprints, the system comprising:
    at least one processor; and
    memory including instructions that, when executed by the at least one processor, cause the at least one processor to perform operations to:
        determine a gap in data collected from a wearable device of a user;
        obtain a set of outputs from a plurality of sensors external to the wearable device, wherein the set of outputs includes vibration data, location data, and electro-magnetic data;
        identify an exercise device based on a location in the location data and an electromagnetic signature near the location in the electro-magnetic data;
        calculate a vibration signature for the exercise device using the vibration data;
        generate a fingerprint using the set of outputs, the fingerprint corresponding to an activity observed by the plurality of sensors, wherein the generated fingerprint is a computer interpretable identifier, and wherein the generated fingerprint includes the vibration signature of the exercise device, the location, and the electro-magnetic signature near the location;
        predict a caloric expenditure activity for the user based on a comparison between the generated fingerprint and a set of fingerprints stored in a database, each fingerprint of the set of fingerprints corresponding to a respective caloric expenditure for a respective caloric expenditure activity, wherein the comparison includes interpreting, via the at least one processor, the generated fingerprint and the set of fingerprints, and wherein the interpreting includes determining if the vibration signature of the exercise device matches the caloric expenditure activity;
        calculate a caloric expenditure for the activity based on the caloric expenditure activity; and
        update an exercise profile of the user associated with the wearable device using the caloric expenditure to fill the gap in data.

2. The system of claim 1, the memory further comprising instructions that, when executed by the at least one processor, cause the at least one processor to perform operations to:
    identify that the generated fingerprint does not match a fingerprint of the set of fingerprints;
    determine a caloric expenditure corresponding to the generated fingerprint; and
    store, in the database, the generated fingerprint and the corresponding calculated caloric expenditure.

3. The system of claim 1, the memory further comprising instructions that, when executed by the at least one processor, cause the at least one processor to perform operations to:
    extract features from each sensor of the plurality of sensors included in the set of outputs to generate a fingerprint vector for each sensor of the plurality of sensors over a time period; and
    merge the fingerprint vector for each sensor to form an aggregate fingerprint vector for the time period; and
    generate the fingerprint using the aggregate fingerprint vector.

4. The system of claim 3, the memory further comprising instructions that, when executed by the at least one processor, cause the at least one processor to perform operations to use pattern matching to find a similarity between a first feature extracted from a first sensor of the plurality of sensors and a second feature extracted from a second sensor of the plurality of sensors.

5. The system of claim 1, the memory further comprising instructions that, when executed by the at least one processor, cause the at least one processor to perform operations to:
    receive a context associated with the activity; and
    adjust the caloric expenditure based on the context.

6. The system of claim 1, the memory further comprising instructions that, when executed by the at least one processor, cause the at least one processor to perform operations to:
    obtain user attributes from the exercise profile of the user; and
    adjust the caloric expenditure using the user attributes.

7. The system of claim 1, the memory further comprising instructions that, when executed by the at least one processor, cause the at least one processor to perform operations to:
    receive a set of data from a smart exercise device; and
    adjust the caloric expenditure using the set of data.

8. The system of claim 1, the memory further comprising instructions that, when executed by the at least one processor, cause the at least one processor to perform operations to:
provide a training mode graphical user interface on a mobile device;
obtain an indication, via the training mode graphical user interface, that an activity has commenced;
receive a set of outputs from at least one sensor in a wearable device;
generate a training fingerprint for the set of outputs; and
store the training fingerprint in the database.

9. At least one non-transitory machine readable medium including instructions for tracking caloric expenditure using sensor driven fingerprints that, when executed by at least one processor, cause the at least one processor to perform operations to:
determine a gap in data collected from a wearable device of a user;
obtain a set of outputs from a plurality of sensors external to the wearable device, wherein the set of outputs includes vibration data, location data, and electro-magnetic data;
identify an exercise device based on a location in the location data and an electromagnetic signature near the location in the electro-magnetic data;
calculate a vibration signature for the exercise device using the vibration data;
generate a fingerprint using the set of outputs, the fingerprint corresponding to an activity observed by the plurality of sensors, wherein the generated fingerprint is a computer interpretable identifier, and wherein the generated fingerprint includes the vibration signature of the exercise device, the location, and the electro-magnetic signature near the location;
predict a caloric expenditure activity for the user based on a comparison between the generated fingerprint and a set of fingerprints stored in a database, each fingerprint of the set of fingerprints corresponding to a respective caloric expenditure for a respective caloric expenditure activity, wherein the comparison includes interpreting, via the at least one processor, the generated fingerprint and the set of fingerprints, and wherein the interpreting includes determining if the vibration signature of the exercise device matches the caloric expenditure activity;
calculate a caloric expenditure for the activity based on the caloric expenditure activity; and
update an exercise profile of the user associated with the wearable device using the caloric expenditure to fill the gap in data.

10. The at least one non-transitory machine readable medium of claim 9, wherein the instructions to compare the generated fingerprint to the set of fingerprints and calculate the caloric expenditure includes instructions to:
identify that the generated fingerprint does not match a fingerprint of the set of fingerprints;
determine a caloric expenditure corresponding to the generated fingerprint; and
store, in the database, the generated fingerprint and the corresponding calculated caloric expenditure.

11. The at least one non-transitory machine readable medium of claim 9, wherein the instructions to generate the fingerprint includes instructions to:
extract features from each sensor of the plurality of sensors included in the set of outputs to generate a fingerprint vector for each sensor of the plurality of sensors over a time period; and
merge the fingerprint vector for each sensor to form an aggregate fingerprint vector for the time period; and
generate the fingerprint using the aggregate fingerprint vector.

12. The at least one non-transitory machine readable medium of claim 11, wherein the instructions to merge the fingerprint vector for each sensor includes instructions to use pattern matching to find a similarity between a first feature extracted from a first sensor of the plurality of sensors and a second feature extracted from a second sensor of the plurality of sensors.

13. The at least one non-transitory machine readable medium of claim 9, further comprising instructions to:
receive a context associated with the activity; and
adjust the caloric expenditure based on the context.

14. The at least one non-transitory machine readable medium of claim 9, further comprising instructions to:
obtain user attributes from the exercise profile of the user; and
adjust the caloric expenditure using the user attributes.

15. The at least one non-transitory machine readable medium of claim 9, further comprising instructions to:
receive a set of data from a smart exercise device; and
adjust the caloric expenditure using the set of data.

16. The at least one non-transitory machine readable medium of claim 9, further comprising instructions to:
provide a training mode graphical user interface on a mobile device;
receive a set of outputs from at least one sensor in a wearable device;
obtain an indication, via the training mode graphical user interface, that an activity has commenced;
generate a training fingerprint for the set of outputs; and
store the training fingerprint in the database.

17. A method for tracking caloric expenditure using sensor driven fingerprints, the method comprising:
determining a gap in data collected from a wearable device of a user;
obtaining a set of outputs from a plurality of sensors external to the wearable device, wherein the set of outputs includes vibration data, location data, and electro-magnetic data;
identifying an exercise device based on a location in the location data and an electromagnetic signature near the location in the electro-magnetic data;
calculating a vibration signature for the exercise device using the vibration data;
generating, using at least one processor, a fingerprint using the set of outputs, the fingerprint corresponding to an activity observed by the plurality of sensors, wherein the generated fingerprint is a computer interpretable identifier, and wherein the generated fingerprint includes the vibration signature of the exercise device, the location, and the electro-magnetic signature near the location;
predicting, using at least one processor, a caloric expenditure activity for the user based on a comparison between the generated fingerprint and a set of fingerprints stored in a database, each fingerprint of the set of fingerprints corresponding to a respective caloric expenditure for a respective caloric expenditure activity, wherein the comparison includes interpreting, via at least one processor, the generated fingerprint and the set of fingerprints, and wherein the interpreting includes determining if the vibration signature of the exercise device matches the caloric expenditure activity;

calculating, using at least one processor, a caloric expenditure for the activity based on the caloric expenditure activity; and updating an exercise profile of the user associated with the wearable device using the caloric expenditure to fill the gap in data.

18. The method of claim 17, wherein comparing the generated fingerprint to the set of fingerprints includes:

identifying that the generated fingerprint does not match a fingerprint of the set of fingerprints;

determining a caloric expenditure corresponding to the generated fingerprint; and storing, in the database, the generated fingerprint and the corresponding calculated caloric expenditure.

19. The method of claim 17, wherein generating the fingerprint includes:

extracting features from each sensor of the plurality of sensors included in the set of outputs to generate a fingerprint vector for each sensor of the plurality of sensors over a time period; and merging the fingerprint vector for each sensor to form an aggregate fingerprint vector for the time period; and generating the fingerprint using the aggregate fingerprint vector.

20. The method of claim 19, wherein merging the fingerprint vector for each sensor includes using pattern matching to find a similarity between a first feature extracted from a first sensor of the plurality of sensors and a second feature extracted from a second sensor of the plurality of sensors.

21. The method of claim 17, further comprising:
receiving a context associated with the activity; and
adjusting the caloric expenditure based on the context.

22. The method of claim 17, further comprising:
obtaining user attributes from the exercise profile of the user; and
adjusting the caloric expenditure using the user attributes.

23. The method of claim 17, further comprising:
receiving a set of data from a smart exercise device; and
adjusting the caloric expenditure using the set of data.

24. The method of claim 17, further comprising:
providing a training mode graphical user interface on a mobile device;
receiving a set of outputs from at least one sensor in a wearable device;
obtaining an indication, via the training mode graphical user interface, that an activity has commenced;
generating a training fingerprint for the set of outputs; and
storing the training fingerprint in the database.

* * * * *